United States Patent

Ueno et al.

[11] Patent Number: 6,133,475
[45] Date of Patent: Oct. 17, 2000

[54] PROCESS FOR PRODUCING 2-HYDROXYNAPHTHALENE-3,6-DICARBOXYLIC ACID

[75] Inventors: Ryuzo Ueno, Nishinomiya; Masaya Kitayama, Takarazuka; Yoshiro Uchiyama, Sanda; Syungo Nara, Kawanishi, all of Japan

[73] Assignee: Kabushiki Kaisha Ueno Seiyaku Oyo Kenkujo, Osaka, Japan

[21] Appl. No.: 09/091,289

[22] Filed: Jun. 16, 1998

[30] Foreign Application Priority Data

Oct. 21, 1996 [JP] Japan .................................. 8-277801

[51] Int. Cl.$^7$ .................................................. C07C 51/15
[52] U.S. Cl. ........................................... 562/424; 562/425
[58] Field of Search .................................... 562/425, 424

[56] References Cited

U.S. PATENT DOCUMENTS

| | | | |
|---|---|---|---|
| 1,593,816 | 7/1926 | Andre | 562/425 |
| 3,405,169 | 10/1968 | Levy et al. | 562/425 |
| 4,287,357 | 9/1981 | Mueller et al. | 562/425 |
| 4,329,494 | 5/1982 | Montgomery | 562/425 |
| 5,075,496 | 12/1991 | Pugach et al. | 562/425 |
| 5,312,976 | 5/1994 | Hautzel et al. | 562/425 |
| 5,532,406 | 7/1996 | Rittner | 562/424 |

*Primary Examiner*—Gary Geist
*Assistant Examiner*—Taylor V. Oh
*Attorney, Agent, or Firm*—Sughrue, Mion, Zinn, Macpeak & Seas, PLLC

[57] ABSTRACT

The present invention relates to a process for preparing 2-hydroxynaphthalene-3,6-dicarboxylic acid which comprises reacting potassium 2-naphtholate and carbon dioxide at a temperature 290° C. or higher under a pressure 30 kg/cm$^2$ (G) or higher. According to this process, 2-hydroxynaphthalene-3,6-dicarboxylic acid can be obtained in high yield.

19 Claims, No Drawings

PROCESS FOR PRODUCING 2-HYDROXYNAPHTHALENE-3,6-DICARBOXYLIC ACID

TECHNICAL FIELD

The present invention relates to an improved process for preparing 2-hydroxynaphthalene-3,6-dicarboxylic acid.

BACKGROUND OF THE INVENTION

It is known for a long time to prepare an aromatic hydroxycarboxylic acid by Kolbe-Schmitt reaction. Although German Patent No. 663,774 discloses an example of a process for preparing 2-hydroxynaphthalene-3,6-dicarboxylic acid from 2-hydroxynaphthalene-6-carboxylic acid, this process is not a method wherein dicarboxylic acid can be prepared directly from 2-hydroxynaphthalene.

Although Japanese Patent Publication (KOKAI) No. 197244/1982 discloses a process for preparing 2-hydroxynaphthalene-3-carboxylic acid (preferred reaction temperature is described as 240–280° C.), it does not refer to the preparation of 2-hydroxynaphthalene-3,6-dicarboxylic acid.

Japanese Patent Publication (KOKAI) No. 340581/1994 discloses a process for preparing monohydroxynaphthalene carboxylic acid (2-hydroxynaphthalene-3-carboxylic acid and 2-hydroxynaphthalene-6-carboxylic acid) from alkali metal naphtholate by Kolbe-Schmitt reaction. Small amounts of 2-hydroxynaphthalene-3,6-dicarboxylic acid are produced as a by-product in this process wherein a reaction pressure is low (about 10 bar).

A process for preparing 2-hydroxynaphthalene-6-carboxylic acid is described in Japanese Patent Publication (KOKAI) No. 146843/1988. Although characteristic of this process is that the reaction is carried out under pressurized carbon dioxide while the formed water is successively removed from the reaction system, the pressure of the reaction system is 20 kg/cm$^2$ (G) at the most, and 2-hydroxynaphthalene-3,6-dicarboxylic acid is not produced.

DISCLOSURE OF THE INVENTION

The present invention relates to a novel process for preparing 2-hydroxynaphthalene-3,6-dicarboxylic acid in high yield which is expected as a raw material for pigments, dyes, organic photoconductors and the like.

The present invention relates to a process for preparing 2-hydroxynaphthalene-3,6-dicarboxylic acid characterized in that potassium 2-naphthoate and carbon dioxide are reacted at a temperature 290° C. or higher under a pressure 30 kg/cm$^2$ (G) or higher.

Characteristic of the present invention is that 2-hydroxynaphthalene-3,6-dicarboxylic acid can be obtained in high yield by reacting potassium 2-naphthoate and carbon dioxide at specific temperature under comparatively high pressure.

2-Hydroxynaphthalene is used as potassium salt in the present invention. When other alkali metal salts such as sodium salt of 2-hydroxynaphthalene is reacted with carbon dioxide at the specific temperature under the comparatively high pressure employed in the present invention, 2-hydroxynaphthalene-3,6-dicarboxylic acid which is the objective product of the present invention can hardly be obtained.

It is possible to increase yield of the objective product by adding potassium sources other than potassium salt of 2-hydroxynaphthalene to the reaction system. Although potassium carbonate, potassium hydrogen carbonate, alkyl potassium, potassium alcoholate, potassium salt of mineral acid and the like are exemplified as the potassium sources, potassium salts of aromatic hydroxy compounds are particularly preferred from the viewpoint of increasing yields of the objective compounds.

The aromatic hydroxy compounds mean the compounds having one or more hydroxy groups on the aromatic rings, and are exemplified phenol, dihydroxybenzene, trihydroxybenzene, biphenol, hydroquinone, bisphenol, 1-naphthol, naphthalene-2,6-diol and the like. Hydroxybenzenes such as phenol, dihydroxybenzene and trihydroxybenzene are particularly preferred. The aromatic rings may be substituted by one or more of the substituents other than hydroxy group. A lower alkyl group, a lower alkenyl group, a lower alkynyl group, a lower alkoxy group, a halogen atom, a nitro group, an amino group, an acetyl group and the like are exemplified as the substituents. Concrete compounds having (a) substituent(s) on the aromatic ring are methyl phenol, ethyl phenol, hydroxymethyl phenol, trimethylsilyl phenol, fluorophenol, bromophenol, chlorophenol, iodophenol, methoxy phenol, acetyl phenol, dimethyl phenol, methylisopropyl phenol and trimethyl phenol. The lower alkyl group is particularly preferred.

It is convenient to use about 0.1–3.0 moles of the potassium sources per one mole of potassium 2-naphtholate in the reaction system.

The potassium sources and 2-naphthol or potassium 2-naphtholate and, if necessary, reaction medium and the like as mentioned hereinafter may successively be supplied to the reaction system. The reaction may be carried out by a batch method.

Preferred reaction temperature is 290° C. or higher, more preferably 300° C. or higher. When the reaction temperature becomes 290° C. or higher, the yields of 2-hydroxynaphthalene-3,6-dicarboxylic acid increase suddenly. When the reaction temperature is lower than 290° C., the amounts of 2-hydroxynaphthalene-3-carboxylic acid increase.

It is preferable to set the reaction pressure to 30 kg/cm$^2$ (G) or higher, more preferably 40 kg/cm$^2$ (G) or higher in order to increase the yields of 2-hydroxynaphthalene-3,6-dicarboxylic acid. When the reaction pressure becomes less than 30 kg/cm$^2$ (G), the amounts of 2-hydroxynaphthalene-6-carboxylic acid increase. The reaction pressure may be adjusted by an introducing pressure of carbon dioxide.

The reaction may be carried out in a reaction medium.

Suitable reaction media are aliphatic, alicyclic or aromatic hydrocarbons, and ethers having the residual radicals of these hydrocarbons. The following reaction media are exemplified: light oil, kerosine, lubricating oil, white oil, alkylbenzenes, alkylnaphthalenes, diphenyls, diphenylalkanes, alkyldiphenyls, triphenyls, hydrogenated triphenyls, diphenyl ethers, alkylphenyl ethers, alkyldiphenyl ethers and the mixture thereof. Boiling points of the reaction media may be ordinarily 150–400° C., preferably about 180–400° C. Specific gravities of the reaction media at a room temperature are ordinarily about 0.6–1.5, preferably about 0.7–1.4. The amount of the reaction media to be used is ordinarily about 0.5–10 times by weight, preferably about 1–5 times by weight in relation to that of potassium 2-naphtholate.

The reaction may be carried out as removing the by-products from the reaction system by means of the following methods:

(1) The gas in the reaction system is occasionally removed and pressurized carbon dioxide are newly introduced during the reaction.
(2) The gas in the reaction system is successively removed while the pressurized carbon dioxide is introduced during the reaction in order not to decrease the pressure in the reaction system. In this method, the removal of the by-product to the outside of the reaction system as well as the reaction are accelerated by dispersing the pressurized carbon dioxide into the reaction liquid.
(3) The gas in the reaction system is condensed by a cooler, and the condensate is removed to the outside of the reaction system.

In order to obtain 2-hydroxynaphthalene-3,6-dicarboxylic acid from the reaction mixture, precipitation with acid, washing with water and solvent extraction may suitably be combined.

The present invention will be illustrated by the following examples.

EXAMPLE 1

331 g of 55% aqueous solution of potassium 2-naphtholate and 273 g of TS-900 (available from Shinnittetsu Kagaku Inc: hydrogenated triphenyl) were charged into an autoclave (1 liter) and dehydrated at 260° C. under agitation, and then reacted at 300° C. under 55 kg/cm$^2$ (G) of pressurized carbon dioxide for 2 hours under agitation.

After conclusion of the reaction, the reaction mixture was analyzed by means of liquid chromatography [UV detector: Waters 486 (229 nm); column: Wakosil-II 5C18 (4.6 mm×150 mm, 40° C.). Yield of 2-hydroxynaphthalene-3,6-dicarboxylic acid based on 2-naphthol was 24.2%. Yields of the reaction products are shown in Table 1.

TABLE 1

| Products | Yield (mol %) |
| --- | --- |
| 2-Hydroxynaphthalene-3,6-dicarboxylic acid | 24.2 |
| 2-Hydroxynaphthalene-3-carboxylic acid | 7.9 |
| 2-Hydroxynaphthalene-6-carboxylic acid | 2.8 |

EXAMPLE 2

331 g of 55% aqueous solution of potassium 2-naphtholate, 349 g of 50% aqueous solution of potassium 2,4,6-trimethylphenolate and 626 g of TS-900 were charged into an autoclave (1 liter) and dehydrated at 260° C. under agitation, and then reacted at 300° C. under 55 kg/cm$^2$ (G) of pressurized carbon dioxide for 3 hours under agitation.

After conclusion of the reaction, the reaction mixture was analyzed by means of liquid chromatography according to the same as described in Example 1. Yield of 2-hydroxynaphthalene-3,6-dicarboxylic acid was 42.7% based on 2-naphthol. Yields of the reaction products are shown in Table 2.

TABLE 2

| Products | Yield (mol %) |
| --- | --- |
| 2-Hydroxynaphthalene-3,6-dicarboxylic acid | 42.7 |
| 2-Hydroxynaphthalene-3-carboxylic acid | 3.1 |
| 2-Hydroxynaphthalene-6-carboxylic acid | 4.8 |

EXAMPLE 3

According to the same manner as described in Example 2, the charged mixture was subjected to dehydration.

After the dehydration, the mixture was reacted at 270° C., 280° C., 290° C. or 300° C. under a given agitation, pressurized carbon dioxide [55 kg/cm$^2$ (G)] and reaction time (2 hours).

The reaction mixtures were analyzed according to the same manner as described in Example 1. Yields and proportions of the reaction products are shown in Table 3.

TABLE 3

| Temperature | Yield (mol %) | | | Proportion (%) | | |
| --- | --- | --- | --- | --- | --- | --- |
| (° C.) | A | B | C | A | B | C |
| 270 | 15.5 | 35.1 | 9.6 | 25.7 | 58.3 | 15.9 |
| 280 | 27.0 | 24.5 | 9.1 | 44.6 | 40.4 | 15.0 |
| 290 | 40.2 | 6.4 | 7.5 | 74.3 | 11.8 | 13.9 |
| 300 | 39.6 | 3.8 | 5.9 | 80.3 | 7.7 | 12.0 |

A: 2-hydroxynaphthalene-3,6-dicarboxylic acid
B: 2-hydroxynaphthalene-3-carboxylic acid
C: 2-hydroxynaphthalene-6-carboxylic acid
Proportion (%) = [(A, B or C)/(A + B + C)] × 100

EXAMPLE 4

According to the same manner as described in Example 2, the charged mixture was subjected to dehydration.

After the dehydration, the mixture was reacted at the pressurized carbon dioxide [20 kg/cm$^2$ (G), 30 kg/cm$^2$ (G), 40 kg/cm$^2$ (G) or 55 kg/cm$^2$ (G)] under a given agitation, reaction temperature (300° C.) and reaction time (2 hours).

The reaction mixtures were analyzed according to the same manner as described in Example 1. Yields and proportions of the reaction products are shown in Table 4.

TABLE 4

| Pressure | Yield (mol %) | | | Proportion (%) | | |
| --- | --- | --- | --- | --- | --- | --- |
| (kg/cm$^2$G) | A | B | C | A | B | C |
| 20 | 15.3 | 8.8 | 16.6 | 37.6 | 21.6 | 40.8 |
| 30 | 23.8 | 6.3 | 12.5 | 55.9 | 14.8 | 29.3 |
| 40 | 39.2 | 4.5 | 6.3 | 78.4 | 9.0 | 12.6 |
| 55 | 39.6 | 3.8 | 5.9 | 80.3 | 7.7 | 12.0 |

A: 2-hydroxynaphthalene-3,6-dicarboxylic acid
B: 2-hydroxynaphthalene-3-carboxylic acid
C: 2-hydroxynaphthalene-6-carboxylic acid
Proportion (%) = [(A, B or C)/(A + B + C)] × 100

EXAMPLE 5

According to the same manner as described in Example 2, the charged mixture was subjected to dehydration.

After the dehydration, the mixture was reacted at 55 kg/cm$^2$ (G) of pressurized carbon dioxide for 5 hours under agitation. 2-Hydroxynaphthalene-3,6-dicarboxylic acid was isolated by subjecting the reaction mixture to the conventional post-treatment and purification treatment. Said product was analyzed and identified by means of $^1$H-NMR, $^{13}$C-NMR and IR.

Assignments of $^1$H-NMR, assignments of $^{13}$C-NMR and the typical absorption bands of IR are shown in Table 5, Table 6 and Table 7 respectively.

The analytical instruments used are as follows:
Nuclear magnetic resonance spectrometer Jemini-200 manufactured by Varian Inc.; DMSO-do=5/4(V/U)
Fourier transform infrared spectrophotometer 1650 Type FT-IR manufactured by Perkin-Elmer Inc.

TABLE 5

(¹H-NMR)

| compound | $\delta_H$ (ppm) | | | | J(Hz) | |
|---|---|---|---|---|---|---|
| | 1-H | 4-H | 5-H | 7-H | $J_{7,8}$ | $J_{5,7}$ |
| 2-hydroxynaphthalene-3,6-dicarboxylic acid | 7.31 | 8.64 | 8.57 | 8.00 | 8.8 | 1.6 |

TABLE 6

(¹³C-NMR)

| compound | $\delta_H$ (ppm) | | | | | J(Hz) | | | | $\delta_H$ (ppm) |
|---|---|---|---|---|---|---|---|---|---|---|
| | 1-C | 2-C | 3-C | 4-C | 4a-C | 5-C | 6-C | 7-C | 8-C | 8a-C | C = 0 |
| 2-hydroxynaphthalene-3,6-dicarboxylic acid | 108.3 | 155.8 | 114.1 | 132.4 | 123.0 | 130.5 | 124.5 | 128.4 | 124.4 | 137.8 | 168.8 165.8 |

TABLE 7

(IR)

| $\nu$ (cm$^{-1}$) | |
|---|---|
| 1668.2 | C = 0 |
| 3038.0(B) | OH |

COMPARATIVE EXAMPLE 331 g of 55% aqueous solution of sodium 2-naphtholate, 349 g of 50% aqueous solution of sodium 2,4,6-trimethylphenolate and 626 g of TS-900 were charged into an autoclave (1 liter) and dehydrated at 260° C. under agitation.

After the dehydration, the mixture was reacted at 290° C. under 45 kg/cm² (G) of pressurized carbon dioxide for 2 hours.

After the conclusion of the reaction, the reaction mixture was analyzed by means of liquid chromatography according to the same manner as described in Example 1. 2-Hydroxynaphthalene-3,6-dicarboxylic acid could not be detected. Yields of the reaction products are shown in Table 8.

TABLE 8

| Products | Yield (mol %) |
|---|---|
| 2-Hydroxynaphthalene-3,6-dicarboxylic acid | 0.0 |
| 2-Hydroxynaphthalene-3-carboxylic acid | 2.7 |
| 2-Hydroxynaphthalene-6-carboxylic acid | 0.3 |

INDUSTRIAL APPLICABILITY

According to the present invention, 2-hydroxynaphthalene-3,6-dicarboxylic acid can be prepared in high yield.

What is claimed is:

1. A process for preparing 2-hydroxynaphthalene-3,6-dicarboxylic acid characterized in that potassium 2-naphtholate and carbon dioxide are reacted at a temperature 290° C. to 400° C. under a pressure of at least 30 kg/cm² (G) and that the yield of 2-hydroxynaphthalene3,6-dicarboxylic acid based on 2-naphthalene is at least 24.2%.

2. The process of claim 1, wherein said reaction is carried out in the presence of a reaction medium.

3. The process of claim 2, wherein said reaction medium is selected from the group consisting of aliphatic hydrocarbons, alicyclic hydrocarbons, aromatic hydrocarbons and ethers having residual radicals of these hydrocarbons.

4. The process of claim 1, wherein said reaction is carried out in the presence of a potassium source other than potassium 2-naphtholate.

5. The process of claim 4, wherein said potassium source is a potassium salt of aromatic hydroxy compounds.

6. The process of claim 5, wherein said aromatic hydroxy compounds are hydroxybenzenes.

7. The process of claim 1, wherein the proportion of 2-hydroxynaphthalene-3,6-dicarboxylic acid as a total of proportions of 2-hydroxynaphthalene-3,6-dicarboxylic acid, 2-hydroxynaphthalene-3-carboxylic acid and 2-hydroxynaphthalene-6-carboxylic acid is at least 69.3%.

8. The process of claim 4, wherein the yield of 2-hydroxynaphthalene-3,6-dicarboxylic acid is at least 40.2%.

9. The process of claim 4, wherein the proportion of 2-hydroxynaphthalene-3,6-dicarboxylic acid as a total of proportions of 2-hydroxynaphthalene-3,6-dicarboxylic acid, 2-hydroxynaphthalene-3-carboxylic acid and 2-hydroxynaphthalene-6-carboxylic acid is at least 74.3%.

10. The process of claim 4, wherein the proportion of 2-hydroxynaphthalene-3,6-dicarboxylic acid as a total of proportions of 2-hydroxynaphthalene-3,6-dicarboxylic acid, 2-hydroxynaphthalene-3-carboxylic acid and 2-hydroxynaphthalene-6-carboxylic acid is at least 80.3%.

11. In a process for preparing 2-hydroxynaphthalene-3,6-dicarboxylic acid by reacting alkali metal 2-naphtholate with carbon dioxide, the improvement for obtaining a high yield of the 2-hydroxynaphthalene-3,6-dicarboxylic acid comprising carrying out the reaction with potassium-2-naphtholate at 290° C. to 400° C. and at a pressure of at least 30 kg/cm² (G), wherein the yield of 2-hydroxynaphthalene-3,6-dicarboxylic acid based on 2-naphthalene is at least 24.2%.

12. A process for preparing 2-hydroxynaphthalene-3,6-dicarboxylic acid characterized in that potassium 2-naphtholate and carbon dioxide are reacted at a temperature 290° C. to 400° C. under a pressure of at least 30 kg/cm2 (G) and that the proportion of 2-hydroxynaphthalene-3,6-dicarboxylic acid as a total of proportions of 2-hydroxynaphthalene-3,6-dicarboxylic acid, 2-hydroxynaphthalene-3-carboxylic acid and 2-hydroxynaphthalene-6-carboxylic acid is at least 55.9%.

13. In a process for preparing 2-hydroxynaphthalene-3, 6-dicarboxylic acid by reciting alkali metal 2-naphtholate with carbon dioxide, the improvement for obtaining a high yield of the 2-hydroxynaphthalene-3,6-dicarboxylic acid comprising carrying out the reaction with potassium-2- naphtholate at 290° C. to 400° C. and at a pressure at least 30 kg/cm² (G), and that the proportion of 2-hydroxynaphthalene-3,6-dicarboxylic acid as a total of proportions of 2-hydroxynaphthalene-3,6-dicarboxylic acid, 2-hydroxynaphthalene-3-carboxylic acid, and 2-hydroxynaphthalene-6-carboxylic acid is at least 55.9%.

14. The process of claim 12, wherein said reaction is carried out in the presence of a reaction medium.

15. The process of claim 14, wherein said reaction medium is selected from the group consisting of aliphalic hydrocarbons, alicyclic hydrocarbons, aromatic hydrocarbons and ethers having residual radicals of these hydrocarbons.

16. The process of claim 12, wherein said reaction is carried out in the presence of a potassium source other than potassium 1-naphtholate.

17. The process of claim 16, wherein said potassium source is a potassium salt of aromatic hydroxy compounds.

18. The process of claim 17, wherein said aromatic hydroxy compounds are hydroxybenzenes.

19. The process of claim 12, wherein the proportion of 2-hydroxynaphthalene-3,6-dicarboxylic acid as a total of proportions of 2-hydroxynaphthalene-3,6-dicarboxylic acid, 2-hydroxynaphthalene-3-carboxylic acid and 2-hydroxynaphthalene-6-carboxylic acid is at least 78.4%.

* * * * *

UNITED STATES PATENT AND TRADEMARK OFFICE
CERTIFICATE OF CORRECTION

PATENT NO. : 6,133,475
DATED : October 17, 2000
INVENTOR(S) : Ueno, Ryuzo et al.

It is certified that error appears in the above-identified patent and that said Letters Patent is hereby corrected as shown below:

On the cover of the patent please insert original PCT information --PCT/JP97/03728 filed October 16, 1997--.

Signed and Sealed this

Eighth Day of May, 2001

*Attest:*

NICHOLAS P. GODICI

*Attesting Officer*    Acting Director of the United States Patent and Trademark Office